United States Patent

Noguchi et al.

[11] Patent Number: 5,846,310
[45] Date of Patent: Dec. 8, 1998

[54] COATED SPHERICAL SIO$_2$ PARTICLES

[75] Inventors: Tamio Noguchi; Kazhisa Iwasa, both of Kurosuno, Japan; Ralf Anselmann, Münster, Germany; Martin Knapp, Diebrug, Germany; Manuela Loch, Merxheim, Germany

[73] Assignee: Merck Patent Gesellschaft mit beschrankter Haftung, Darmstadt, Germany

[21] Appl. No.: 845,233

[22] Filed: Apr. 21, 1997

[30] Foreign Application Priority Data

Apr. 22, 1996 [EP] European Pat. Off. ............. 96106278

[51] Int. Cl.$^6$ ....................................................... C09C 1/28
[52] U.S. Cl. .......................... 106/482; 106/446; 106/457; 106/445; 106/490; 428/403; 428/404; 428/405; 424/724
[58] Field of Search ..................................... 106/409, 456, 106/457, 459, 439, 482, 490, 446, 445; 428/403, 404, 405, 406; 424/401, 724

[56] References Cited

U.S. PATENT DOCUMENTS

| | | | |
|---|---|---|---|
| 4,600,646 | 7/1986 | Stout | 428/405 |
| 4,775,520 | 10/1988 | Unger et al. | |
| 4,911,903 | 3/1990 | Unger et al. | |
| 5,139,980 | 8/1992 | Nakahara et al. | |
| 5,512,094 | 4/1996 | Linton | 106/456 |

FOREIGN PATENT DOCUMENTS

| | | |
|---|---|---|
| 275688 | 12/1987 | European Pat. Off. |
| 6-11872 | 2/1994 | Japan. |
| 93/25611 | 6/1993 | WIPO. |

*Primary Examiner*—Michael Marcheschi
*Attorney, Agent, or Firm*—Millen, White, Zelano, & Branigan, P.C.

[57] ABSTRACT

Spherical SiO$_2$ particles with a size of from 5 to 500 nm coated at individual points with TiO$_2$, Fe$_2$O$_3$ or ZrO$_2$ particles with a size of less than 60 nm. The coated SiO$_2$ particles can be aftercoated with silanes or further metal oxides. The products obtained are used for pigmenting paints, printing inks, plastics and coatings or as sunscreen agents.

25 Claims, 3 Drawing Sheets

COATED SPHERICAL SIO$_2$ PARTICLES

BACKGROUND OF THE INVENTION

The invention relates to spherical SiO$_2$ particles coated with oxides of the elements titanium, iron or zircon, to a process for their preparation and to the use of the products obtained.

Spherical SiO$_2$ particles are known per se from the prior art. SiO$_2$ particles are obtained by hydrolytic polycondensation from alcoholate compounds, after which they are also obtained in the form of compact, monodisperse, spherical particles. The fundamental reaction conditions for the preparation of SiO$_2$ particles by hydrolytic poly-condensation can be found, for example, in the publications by W. Stöber et al. in *J. Colloid and Interface Science* 26, 62 (1968) and 30,568 (1969) and in U.S. Pat. No. 3,634,588. The particles thus prepared, however, often show large standard deviations in their particle diameter and have a certain porosity.

For the preparation of highly monodisperse, non-porous, spherical SiO$_2$ particles which have a standard deviation of not more than 5%, reference is made to EP 216,278 (equivalent to U.S. Pat. No. 4,775,520 and U.S. Pat. No. 4,911,903), which discloses a correspondingly oriented preparation process based on hydrolytic polycondensation producing non-porous particles. The key feature of this process, which is preferred for the preparation of the particles according to the present invention, is a two-stage procedure. In this procedure, hydrolytic polycondensation of tetraalkoxy silanes in aqueous-alkaline-ammoniacal medium is first used to form a sol or a suspension of primary particles, which are then brought by metered addition of further tetraalkoxysilane to the desired final size.

An appropriate process for the preparation of various metal oxides in the form of spherical particles with narrow particle size distribution is to be found in EP 275,688 (equivalent to U.S. Pat. No. 4,861,572).

A corresponding two-stage process for the preparation of various metal oxides and also mixed oxides, which, furthermore, also have glycolic groups chemically bonded to the surface, as described in EP 391,447 (equivalent to U.S. Pat. No. 5,139,980).

SiO$_2$ particles organically modified in this way can be used as tailor-made sorbents for chromatography. They are particularly suitable for use in reversed-phase chromatography. The use of these particles allows the separation of high molecular weight biomolecules, such as peptides, proteins or nucleic acids.

The subsequent coating of spherical SiO$_2$ particles with titanium dioxide is described in Japanese Published Specification No. 06-011,872. SiO$_2$ particles with a size of 0.5–50 $\mu$m are coated by suspending them in an aqueous titanyl sulfate solution and heating the suspension, the titanyl sulfate hydrolysing and the resulting titanium oxide hydrate being precipitated onto the SiO$_2$ particles. In this process, the entire surface is coated with titanium dioxide. The weight ratio of silicon dioxide to titanium dioxide is within the range from 10:90 to 90:10.

The size of the individual crystallites within the continuous TiO$_2$ coat is about 500 nm.

The coated SiO$_2$ particles are separated off, washed and dried in accordance with known methods. In order to increase their mechanical strength they are heated at from 500° to 900° C. for from 30 minutes to 5 hours.

The product obtained possesses a high masking capacity and a screening effect towards ultraviolet radiation. It is used in cosmetology as a component of make-up formulations.

The high masking capacity of this product makes it unsuitable for use in sunscreen compositions. A sunscreen composition should possess a high absorption and reflection capacity for ultraviolet radiation but at the same time should be highly transparent to the visible component of sunlight, so that it is not visible on the skin.

SUMMARY OF THE INVENTION

An object of the present invention is to provide a product which consists of spherical SiO$_2$ particles coated at "individual points" with oxide particles of the elements titanium, iron or zircon. The product is to have a high absorption and reflection capacity of for ultraviolet radiation while in contrast being highly transparent to visible light. Furthermore, the product should not have a tendency towards agglomeration, such a tendency being a known feature of conventional UV protection filters, for example, ultrafine titanium dioxide.

A further object of the present invention is to provide a product which is suitable as filler in organic matrix materials, with the refractive index of the particles being adapted as a function of the application to the refractive index of the organic matrix.

Upon further study of the specification and appended claims, further objects and advantages of this invention will become apparent to those skilled in the art.

It has, surprisingly, been found that, by means of a specific procedure, it is possible to coat spherical SiO$_2$ particles, e.g., particles with a size of from about 5 to 500 nm at individual points (i.e., at discrete locations) with oxide particles of the elements titanium, iron or zircon, e.g., particles with a size of less than about 60 nm to give highly transparent products which possess a high absorption and reflection capacity in the ultraviolet region. Preferably, the particles have a mass ratio of SiO$_2$: (TiO$_2$, Fe$_2$O and/or ZrO$_2$) of 1:0.1 to 1:2.

The invention therefore provides spherical SiO$_2$ particles with a size of, e.g., from about 5 to 500 nm, preferably with a size of less than 100 nm, which are coated at individual points with oxide particles of the elements titanium, iron or zircon or mixtures of these metal oxides with a size of, e.g., less than about 60 nm, which coated particles are obtainable, in the case of titanium, for example, by adding a titanium tetrachloride solution, e.g., containing 5–40% TiCl$_4$, at a metering rate of, e.g., from 0.0005 to 0.5 mg of titanium, calculated as TiO$_2$, per minute and per m$^2$ surface area of the SiO$_2$ particles, to an aqueous dispersion of the SiO$_2$ particles, e.g., at a pH of from 1.3 to 2.5, preferably from 1.6 to 2.0, separating off the coated SiO$_2$ particles and subjecting them to drying and, if desired, calcination. (Above and below, where titanium is referenced, it is to be understood that iron, zircon and mixtures thereof are also included.)

The invention additionally provides a process for the preparation of spherical SiO$_2$ particles with a size of from 5 to 500 nm, preferably less than 100 nm, which are coated at individual points with oxide particles of the elements titanium, iron or zircon with a size of less than 60 nm, which is characterized in that the SiO$_2$ particles are dispersed in deionized water at elevated temperature, e.g., of from 50° to 90° C. in a concentration of from 1 to 30% by weight, preferably 5–10% by weight, in case of a coating with TiO$_2$ particles in aqueous titanium salt solution, e.g., with 5–40% by weight salt, is added at a basic pH, e.g., of from 1.3 to 2.5, preferably from 1.6 to 2.0, at a metering rate of, e.g., from 0.0005 to 0.5 mg of titanium, calculated as TiO$_2$, per minute and per m$^2$ surface area of the SiO$_2$ particles, the pH being kept constant by simultaneous addition of a base, the coated SiO$_2$ particles are separated off, washed with water and then with ethanol, are initially dried in air and are then dried in vacuo, e.g., at from 70° to 125° C.

The coated SiO$_2$ particles according to the invention may also be produced in the following way: an aqueous solution of a metal salt, e.g., titanium tetrachloride, is heated, e.g., to 60° C. with stirring. The obtained suspension of the metal oxide is added dropwise to a suspension of spherical SiO$_2$ particles. The pH is adjusted to a low value, e.g., to 2.0 with 32% NaOH solution, with stirring and a silane coupling agent is added to the suspension. After 15 minutes, the pH value is increased, e.g., to 8.0 with 32% NaOH solution, the suspension is stirred again, e.g., for 10 minutes. After filtering, washing and drying the coated SiO$_2$ particles are powdered by using a blender and the obtained powder is calcined, e.g., at 700° C. for 5 minutes.

The invention also provides for the use of the particles according to the invention as sunscreen agents in cosmetic formulations and as fillers in organic matrix materials, e.g., as in WO93/25611. WO93/25611 relates to the use of such particles as refractive index-adapted fillers in polymeric or polymerizable systems, e.g., epoxy resins, which are preferably used as embedding compositions for optical, electrooptical and optoelectronic structural elements. One of the fundamental possible uses is the production of optically homogeneous, lightly transparent polymeric articles. Use-specific adaptation of the refractive index is desirable in this case, meaning that the refractive index of the filler and organic matrix are as far as possible identical. The refractive index of the filler depends on the mass ratio SiO$_2$:TiO$_2$.

Furthermore, the particles are used for pigmenting paints, printing inks, plastics and coatings. In the above utilities, the particles of the invention are used in analogy with conventional silicas.

The spherical SiO$_2$ particles to be used as starting materials can be any known per se from the prior art.

The fundamental reaction conditions for the preparation of SiO$_2$ particles by hydrolytic polycondensation can be found, for example, in the publications by W. Stöber et al. in *J. Colloid and Interface Science* 26, 62 (1968) and 30, 568 (1969) and in U.S. Pat. No. 3,634,588. The particles thus prepared, however, often show large standard deviations in their particle diameter and have a certain porosity.

For the preparation of highly monodisperse, non-porous, spherical SiO$_2$ particles which have a standard deviation of not more than 5%, reference is made to EP 216,278, which discloses a correspondingly oriented preparation process based on hydrolytic polycondensation. The key feature of this process, which is preferred for the preparation of the particles according to the present invention, is a two-stage procedure. In this procedure, hydrolytic polycondensation of tetraalkoxysilanes in aqueous-alkaline-ammoniacal medium is first used to form a sol or a suspension of primary particles, which are then brought by metered addition of further tetraalkoxysilane to the desired final size.

The grain size of the SiO$_2$ particles to be employed as starting material is dependent on the intended use of the SiO$_2$ particles according to the invention which are coated with oxide particles of the elements titanium, iron and zircon. Optimization of size can be routinely performed, dependent on the intended use, by one of ordinary skill in the relevant art.

Particle sizes of between about 5 nm and 500 nm are typical. Sizes of the particles herein refer to diameter. For the use of the products according to the invention as sunscreen agents in cosmetic formulations, for example, particle sizes of from about 5 to 100 nm are typically employed.

For the use as filler in organic matrix materials, particle sizes of from 50 to 500 nm are typically employed. Depending on the choice of the oxides on which the inorganic particles are based, the refractive index of the products according to the invention can be tailored precisely to the refractive index of the organic matrix. Such tailoring is conventional in the art. Polymers or polymerizable systems comprising these particles can be used, for example, as embedding compositions for optical, electrooptical and optoelectrical components. Such embedding compositions exhibit an improved optical homogeneity. Light-emitting diodes produced with such compositions are distinguished inter alia by an enhanced light yield. Further details on this use of the products according to the invention are given in WO 93/25611.

The size of the TiO$_2$, FeO$_3$ and ZrO$_2$ oxide particles on the products according to the invention is, e.g., below 60 nm. Size of the oxides herein refers to the dimension of the particle in its longest dimension.

The proportion of titanium dioxide, iron oxide or zircon oxide in the product according to the invention is, e.g., from about 20 to 75% by weight, preferably from about 40 to 50% by weight.

The products according to the invention can be after-coated with organic and/or inorganic compounds by known methods.

By aftercoating with silanes or metal oxides, it is possible to prevent the agglomeration of the monodisperse particles during the drying process. In the case where the products according to the invention are used as sunscreen agents, it is possible by aftercoating with iron oxide to adjust the color to a defined skin shade. Aftercoating with the zinc oxide increases the effectiveness of the product as a UV-A absorber.

When aftercoating with a silane of the general formula R$_n$Si(OX)$_3$, in which R$_n$ is an alkyl group having 1 to 18 carbon atoms and X is an alkyl group having 1 to 2 carbon atoms, typically from about 0.02 to 2% by weight of the silane, calculated as SiO$_2$, are applied to the product according to the invention. Preference is given to the use of CH$_3$Si(OMe)$_3$.

Preferred metal oxides used for aftercoating are zinc oxide, iron oxide, zirconium oxide and cerium oxide.

Figure 1:
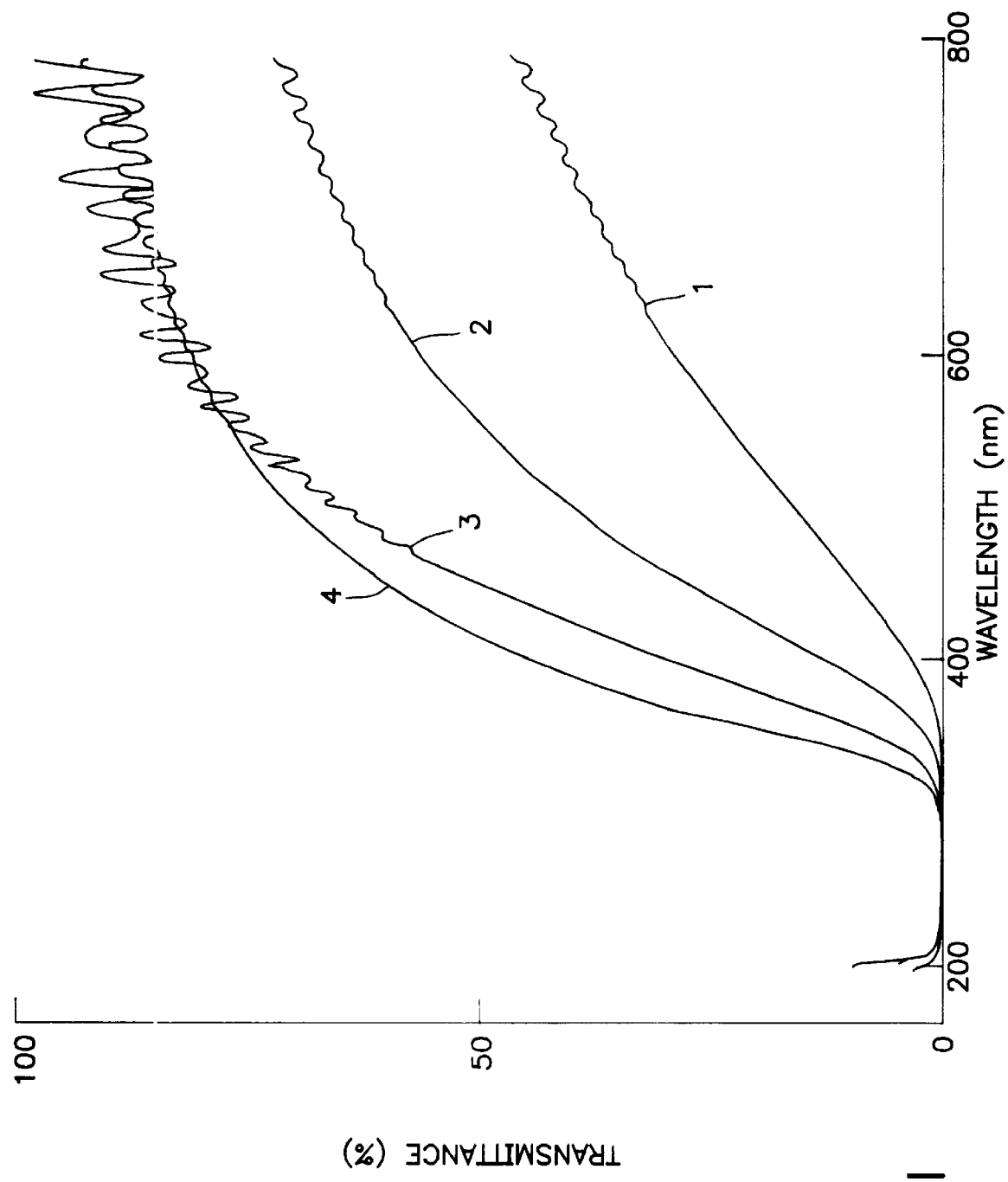
FIG. 1 compares two embodiments of the pigment according to the invention with known sunscreen agents with respect to their transparency in the wavelength range from 220 to 800 nm.
Figure 2:
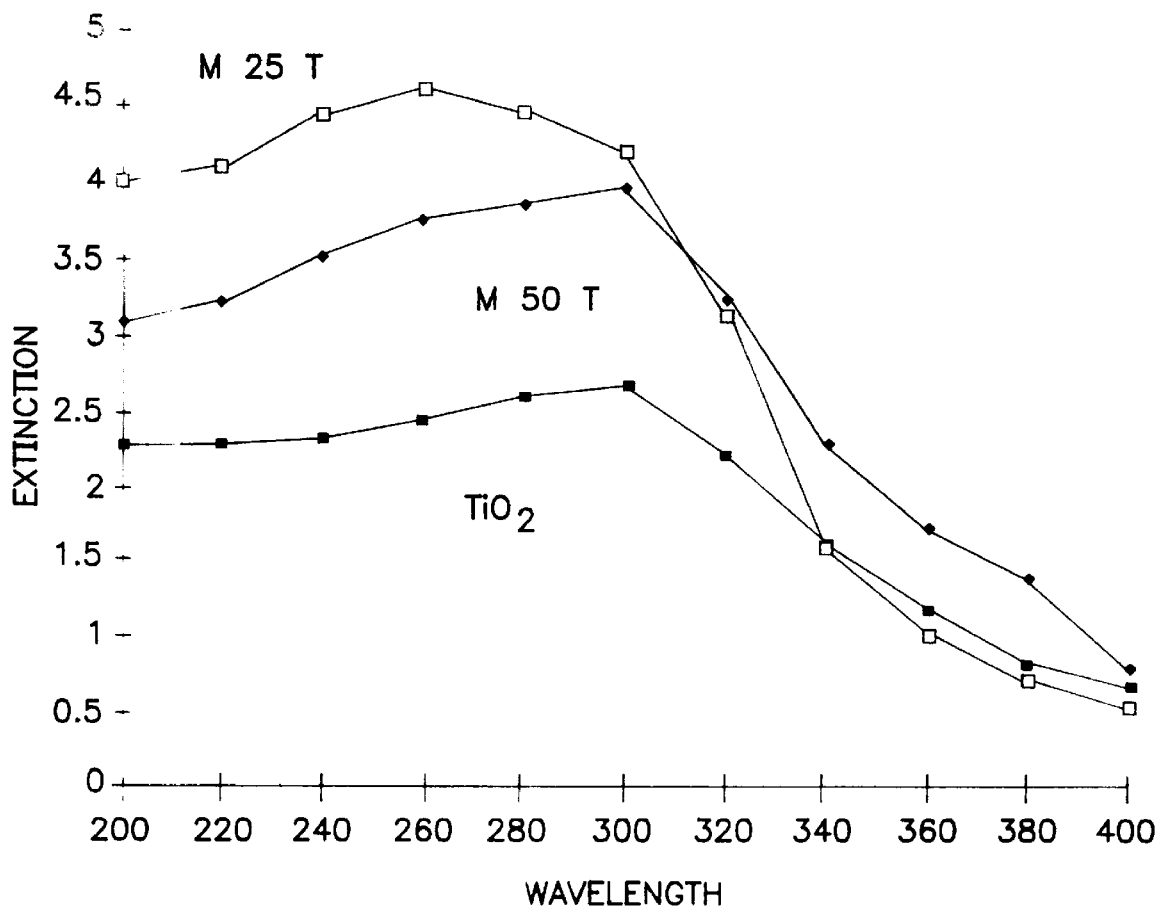
FIG. 2 compares two embodiments of the pigment according to the invention with a known sunscreen agent (ultrafine TiO$_2$) with resect to their extinction in the wavelength range from 200 to 400 nm.
Figure 3A:
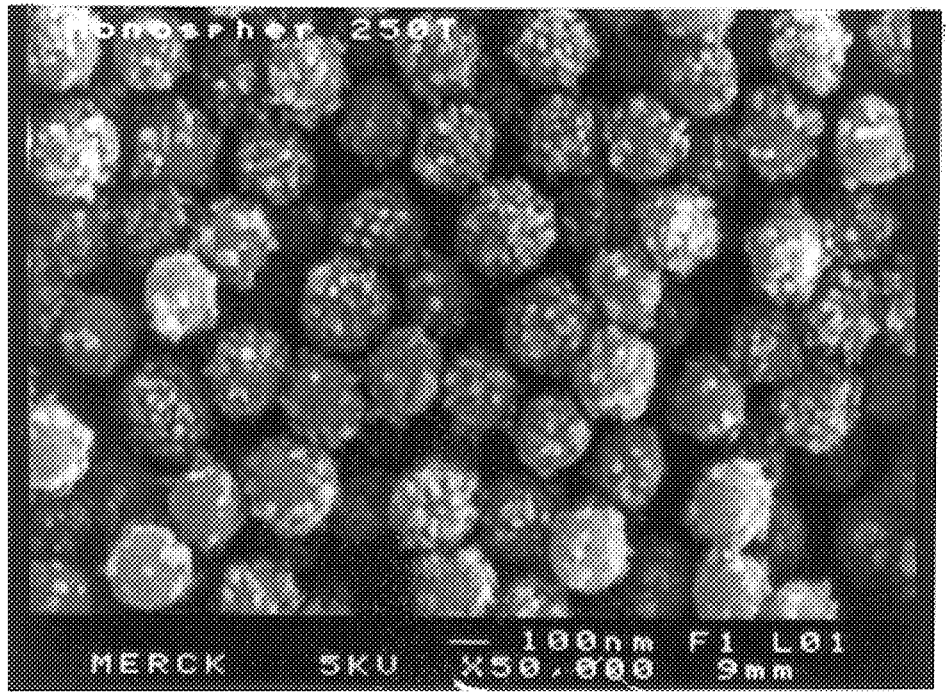
FIGS. 3(a) and 3(b) show SEM micrographs of the products according to the invention.
Figure 3B:
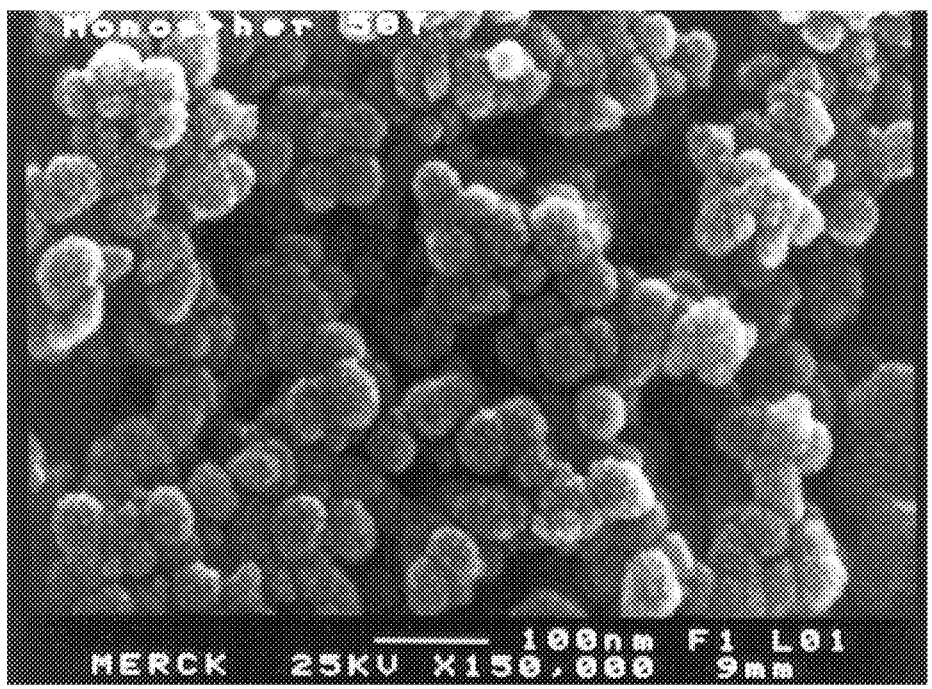

From SEM micrographs of the products according to the invention with two different particle sizes, 250 and 50 nm, it is evident that the titanium, iron or zircon oxide is arranged at individual points, e.g., at discrete locations, on the surface of the SiO$_2$ particles and does not form, as is the case with known products, for example, according to JP 06-011 872 (Kokoku), a continuous coat. Such materials are transparent to visible light, unlike those having a continuous coat of metal oxide.

The concentration of the additionally applied metal oxides is, e.g., from about 1 to 100% by weight, preferably about 10% by weight, based on the content of $TiO_2$.

For the process according to the invention for the preparation of the $SiO_2$ particles coated at individual points with $TiO_2$ particles, it is highly preferable to avoid an excess of titanium salt. This is achieved in that the quantity of titanium salt supplied to the hydrolysis per unit time is only that necessary for uniform formation of the $TiO_2$ particles. This effect is best achieved if the hydrolysis is carried out at a temperature which is as constant as possible and with approximately constant pH.

For example, a 5 to 40% titanium tetrachloride solution is added at a metering rate of from 0.0005 to 0.5 mg of $TiO_2$ per $m^2$ surface area of the $SiO_2$ particles per minute to an aqueous dispersion of the $SiO_2$ particles at a pH of from 1.3 to 2.5, preferably from 1.6 to 2.0.

Since the different fractions of $SiO_2$ particles possess different diameters and therefore different surface areas, the values are different for each particle size when equal quantities are employed, and can be routinely calculated as below:

| Particle Ø in nm | Surface area $m^2/g$ | Min. quantity of $TiO_2$ per $m^2$ per minute | Max. quantity of $TiO_2$ per $m^2$ per minute |
| --- | --- | --- | --- |
| 1000 | 3 | 0.02 mg | 0.5 mg |
| 500 | 6 | 0.01 mg | 0.25 mg |
| 250 | 12 | 0.005 mg | 0.15 mg |
| 100 | 30 | 0.002 mg | 0.05 mg |
| 50 | 60 | 0.001 mg | 0.025 mg |
| 25 | 120 | 0.0005 mg | 0.012 mg |

The $TiCl_4$ solution used preferably has a concentation of 15% by weight of $TiCl_4$ with a density of 1.123 g/ml. The concentration range of the $TiCl_4$ solutions to be used typically extends from 5 to 40% by weight.

In accordance with the process of the invention, it is possible to offer the surfaces to be coated, per unit time, only a small quantity of titanium salt such that all of the titanium dioxide hydrate is able to deposit on the surfaces, and no freely mobile by-products can be formed in the dispersion. Further details are described in U.S. Pat. No. 3,553,001.

The $SiO_2$ particles according to the invention, coated with titanium dioxide, iron oxide or zircon oxide, can, depending on their intended use, be coated with further metal oxides or with organic compounds, for example, silanes, by known methods.

For example, further coating with zinc oxide is likewise carried out by known methods. The zinc oxide hydrate is precipitated by hydrolysis of zinc chloride, e.g., using an ammonium complex at a pH of from 11 to 12. The $SiO_2$ particles according to the invention which are coated with $TiO_2$ particles are suspended, e.g., at room temperature in deionized water, the pH is adjusted, e.g., to 11–12 with ammonia solution, and a prepared zinc chloride solution is then added. By slow heating of the suspension, the ammonia is driven off, the pH of the suspension falls and the zinc oxide hydrate is slowly precipitated. The particles coated with zinc oxide hydrate are separated off, washed, e.g., with water and then with ethanol, and dried, e.g., initially dried in air and then dried in vacua at from 70° to 125° C.

The zinc oxide hydrate can also be precipitated by hydrolyzing zinc oxalate or zinc chloride.

Aftercoating of the particles according to the invention with iron(III) oxide is likewise carried out by known methods; the same applies to aftercoating with zirconium oxide.

For example, in the case of aftercoating with iron(III) oxide, an iron(III) chloride solution is metered, e.g., at a temperature of from 60° to 90° C. and at a pH of from 2.5 to 4.5, into an aqueous suspension of the $SiO_2$ particles according to the invention, coated with titanium dioxide. The pH is kept constant, e.g., by simultaneous addition of 32% sodium hydroxide solution.

The particles coated with iron(III) oxide are separated off, washed, e.g., with water and then with ethanol, and dried, e.g., initially dried in air and then dried in vacuo at from 70° to 125° C.

The pigments according to the invention are preferably dried at temperatures from about 110° to 125° C. under normal pressure or from about 70° to 125° C. in vacuo. Dependent on the purpose, the pigments can be additionally calcined, e.g., at temperatures from about 300° C. to 900° C. for from about 5 to 60 minutes.

The pigments according to the invention are used for pigmenting paints, printing inks, plastics, coatings or as sunscreen agents in cosmetic formulations.

When the pigment according to the invention is used as a sunscreen agent in cosmetic formulations, the pigment is incorporated into the formulation in a concentration of, e.g., up to 5% by weight.

For the comparison shown in FIG. 1, the products were incorporated into VS® medium of Dainichiseika Co. Ltd. in a concentration of 1.5% by weight, and the transparency was measured.

The VS medium contains a copolymer of vinyl chloride and vinyl acetate as main resin and xylene in a concentration of from 30 to 40% and cyclohexanone in a concentration of from 50 to 60%.

Plot 1 shows the transparency of an ultrafine titanium dioxide, while plot 2 shows the transparency of an ultrafine titanium dioxide coated with iron oxide. Plot 3 shows the transparency of a pigment according to the invention having the composition 27% $SiO_2$, 53% $TiO_2$, 20% $Fe_2O_3$. Plot 4 shows the transparency of a pigment according to the invention having the composition 31% $SiO_2$ and 69% $TiO_2$.

The plots show that, in the region of visible light, the pigments according to the invention possess a substantially higher transparency than ultrafine titanium dioxide. This means that ultrafine titanium dioxide causes a white film to appear on the hand, whereas the pigments according to the invention remain invisible on the skin owing to their high transparency.

Table 1 compares the transparency and absorbance of the 4 abovementioned pigments at identical and at different concentrations in the formulation.

TABLE 1

| | | Transmittance % | | | Absorbance | |
| --- | --- | --- | --- | --- | --- | --- |
| Pigment No. | Concentr % by weight | Visible light (550 nm) | UV-A (380 nm) | UV-B (300 nm) | UV-A (380 nm) | UV-B (300 nm) |
| 1 | 1.5 | 22 | 1 | 0 | 2.0 | 3.7 |
| 2 | 1.5 | 76 | 34 | 0 | 0.5 | 2.7 |
| 3 | 1.5 | 49 | 6 | 0 | 1.2 | 3.0 |
| 4 | 1.5 | 75 | 19 | 0 | 0.7 | 2.8 |
| 5 | 0.75 | 66 | 12 | 1 | 0.9 | 2.0 |
| 6 | 3.0 | 64 | 12 | 0 | 0.9 | 3.4 |
| 7 | 1.0 | 63 | 17 | 2 | 0.7 | 1.7 |

TABLE 1-continued

| Pigment No. | Concentr % by weight | Transmittance % | | | Absorbance | |
| --- | --- | --- | --- | --- | --- | --- |
| | | Visible light (550 nm) | UV-A (380 nm) | UV-B (300 nm) | UV-A (380 nm) | UV-B (300 nm) |
| 8 | 2.0 | 62 | 8 | 0 | 1.2 | 3.3 |

Pigments Nos. 1 and 5: Ultrafine $TiO_2$
Pigments Nos. 2 and 6: Invention (31% $SiO_2$, 69% $TiO_2$)
Pigments Nos. 3 and 7: Ultrafine $TiO_2$ + $Fe_2O_3$
Pigments Nos. 4 and 8: Invention (27% $SiO_2$, 53% $TiO_2$, 20% $Fe_2O_3$)

The table shows that pigment No. 2 according to the invention possesses a transparency at 550 nm which is approximately 3.5 times higher than the transparency of ultrafine titanium dioxide (pigment No. 1).

To establish approximately the same transparency, relative to ultrafine titanium dioxide, 4 times the quantity of the pigment according to the invention can be added to a cosmetic formulation. This means that, with the pigment according to the invention, it is possible to achieve a markedly higher light protection effect.

The $SiO_2$ particles coated with $TiO_2$ (particles sizes 25 and 50 nm) show a significantly higher extinction (shielding capability) in the wavelength range from 200 to 320 nm. However, in the range of the visible light the pigments of the invention show the same extinction (transparency) as the ultrafine $TiO_2$.

According to the invention $SiO_2$ as a core particle for newly disclosed pigments is coated with $TiO_2$ particles. Due to the $TiO_2$ particles containing the core $SiO_2$ particles directly, the $TiO_2$ particles act as if they were single particles. Accordingly, the fine particle of $TiO_2$ coated $SiO_2$ pigment has superior transmittance and great UV ray shielding capability. This newly developed pigment can be contained in high concentration in a sunscreen product because of such superior transparency producing an excellent sunscreen which has high UV-ray shielding capability.

In addition, the $Fe_2O_3$ type pigment is treated with iron oxide on the surface of $TiO_2$ coated colloidal silica particles. For UV-A&B range, $Fe_2O_3$ has also shielding capability, so this iron oxide type pigment has higher UV-A&B shielding capability compared with $TiO_2$ type pigment because of the efficacy of combination $TiO_2$ and $Fe_2O_3$. With the addition, the pigment coloring to skin-tone can be get by the content of iron oxide. Sunscreen products with several skin tone in cosmetics can be produced.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application European No. 96106278.3, filed Apr. 22, 1996, are hereby incorporated by reference.

EXAMPLES

Example 1

3000 g of an aqueous dispersion of $SiO_2$ particles with a size of 250 nm (5% by weight $SiO_2$) are heated to 75° C. with stirring. 198 g of 60% $TiCl_4$ solution are diluted with 141 g of deionized water and metered at a metering rate of 1.5 ml/min into the dispersion. By simultaneous addition of 32% NaOH solution, the pH is kept constant at 2.2. After 60 minutes, the metering rate of the $TiCl_4$ solution is increased to 3 ml/min. Metered addition of the $TiCl_4$ solution is complete after 110 minutes. The reaction mixture is then stirred for a further 15 minutes and neutralized with NaOH solution, and the solid is separated off, washed free from salt, then washed with 0.5 l of ethanol and, after initial drying in air, is dried overnight in a vacuum drying cabinet at from 70° to 75° C. The $TiO_2$ content of the pigment is 25% by weight.

Example 2

3000 g of an aqueous dispersion of $SiO_2$ particles with a size of 250 nm (5% by weight $SiO_2$) are heated to 75° C. with stirring. 350 g of iron(III) chloride solution (15% by weight Fe, Merck Art. 5513) are diluted with 306 g of deionized water to an iron content of 8% by weight. The solution is metered into the dispersion at 0.5 ml/min. After 10 minutes, the rate is increased to 1.0 ml/min and, after a further 10 minutes, to 1.5 ml/min. This rate is maintained until the end of coating. By simultaneous addition of 32% sodium hydroxide solution, the pH is kept constant at between 3.2 and 3.3. Addition is complete after about 6 hours. After the end of the addition of $FeCl_3$, stirring is continued for 15 minutes and the mixture is then neutralized with the NaOH solution. The solid is separated off, washed free from salt, washed with 0.5 l of ethanol and finally, after initial drying in air, is dried overnight in a vacuum drying cabinet at 70°–75° C. The $Fe_2O_3$ content of the finished pigment, based on oxides ($SiO_2$ and $Fe_2O_3$), is 33% by weight.

Example 3

$SiO_2$ particles with a size of 250 nm are coated with $TiO_2$ in accordance with Example 1. The dispersion is then adjusted to a pH of 3.2 using NaOH solution. 11.5 g of iron(III) chloride solution (15% by weight Fe, Merck Art. 5513) are diluted with 46.9 g of water to an iron content of 3% by weight and metered at a rate of 0.5 ml/min into the abovementioned dispersion. After 60 minutes, the rate of metering is increased to 1.0 ml/min. Addition is complete after about 90 minutes. During the addition of the iron chloride solution, the pH is held between 3.2 and 3.3 by simultaneous addition of NaOH solution. The reaction mixture is then stirred for a further 15 minutes and neutralized with NaOH solution, and the solid is separated off, washed free from salt, then washed with 0.5 l of ethanol and, after initial drying in air, is dried overnight in a vacuum drying cabinet at from 70° to 75° C. The iron content of the pigment is 5% by weight $Fe_2O_3$, based on the $TiO_2$ content of the pigment.

Example 4

2400 g of an aqueous dispersion of $SiO_2$ particles with a size of 250 nm (5% by weight $SiO_2$) are heated to 75° C. with stirring. 160 g of 60% $TiCl_4$ solution are diluted with 112 g of deionized water, and 6.8 g of zinc chloride are added to the solution with stirring and dissolved. This solution is metered at a rate of 1.2 ml/min into the abovementioned dispersion, the pH being kept constant at from 2.2 to 2.3 by simultaneous addition of NaOH solution. After 60 minutes, the rate of metering is increased to 2.4 ml/min. Addition is complete after about 110 minutes. The reaction mixture is subsequently stirred for a further 15 minutes and neutralized over the course of 25 minutes with the aid of an NaOH solution. To ensure complete precipitation of the zinc hydroxide, the dispersion is subsequently stirred for 30 minutes and then allowed to cool to room temperature. The solid is then separated off, washed free from salt, then washed with 0.5 l of ethanol and, after initial drying in air, is dried overnight in a vacuum drying cabinet at from 70° to 75° C. The zinc oxide content of the pigment is 10% by weight, based on the $TiO_2$ content of the pigment.

Example 5

2400 g of an aqueous dispersion of $SiO_2$ particles with a size of 250 nm (5% by weight $SiO_2$) are heated to 75° C. with stirring. 160 g of 60% $TiCl_4$ solution are diluted with 112 g of deionized water and metered at a rate of 1.2 ml/min into the abovementioned dispersion, the pH being kept constant at from 2.2 to 2.3 by simultaneous addition of NaOH solution. After 60 minutes, the rate of metering is increased to 2.4 ml/min. Addition is complete after about 110 minutes. The reaction mixture is subsequently stirred for a further 15 minutes and neutralized over the course of 25 minutes with the aid of an NaOH solution. Subsequently, a zinc chloride solution and an oxalic acid solution are metered, simultaneously but separately from one another, each at a rate of 1.2 ml/min into the neutralized reaction mixture, the pH being kept constant at 7 by simultaneous addition of an NaOH solution. The zinc chloride solution contains 6.8 g of zinc chloride in 61 g of water. The oxalic acid solution contains 6.3 g of oxalic acid in 61 g of water. Addition is complete after about 55 minutes. To ensure complete precipitation of the zinc oxide, the dispersion is subsequently stirred and then allowed to cool to room temperature. The solid is separated off, washed free from salt, then washed with 0.5 l of ethanol and, after initial drying in air, is dried overnight in a vacuum drying cabinet at from 70° to 75° C. The zinc oxide content of the pigment is 10% by weight, based on the $TiO_2$ content of the pigment.

Example 6

3000 g of an aqueous dispersion of $SiO_2$ particles with a size of 250 nm (5% by weight $SiO_2$) are heated to 75° C. with stirring.

198 g of 60% $TiCl_4$ solution are diluted with 142 g of deionized water and metered at a metering rate of 1.5 ml/min into the dispersion. By simultaneous addition of 32% NaOH solution, the pH is kept constant at 2.2. After 60 minutes, the metering rate of the $TiCl_4$ solution is increased to 3 ml/min. Metered addition of the $TiCl_4$ solution is complete after 110 minutes. The reaction mixture is then stirred for a further 15 minutes and neutralized with NaOH solution.

Using 25% ammonia solution, the pH of the dispersion is adjusted to 11–12, and a zinc chloride solution consisting of 8.4 g of zinc chloride in 162 g of deionized water is added. By slow heating of the dispersion, the ammonia is driven off and the zinc hydroxide is precipitated. The precipitation end point is reached when the addition of dilute hydrochloric acid to a filtered sample of the dispersion no longer produces a precipitate. After cooling to room temperature, the solid is worked up in accordance with Example 5.

The zinc oxide content of the pigment is 10% by weight, based on the $TiO_2$ content.

Example 7

66 g (20 g as $SiO_2$) of colloidal silica sol, type ST-S, with a size distribution of 5 to 9 nm in 500 ml of deionized water are heated to 80° C. with stirring. The pH is rapidly adjusted to 1.6 with conc. HCl. Then 256 ml (45 g as $TiO_2$) of $TiCl_4$ solution (418 g/l) are metered in over about 7 hours, while maintaining the pH at 1.6 using 32% NaOH solution. After stirring the suspension for 15 minutes, the pH is adjusted to 3.0 with 32% NaOH, and 3.3 g of silane coupling agent, $CH_3Si(OMe)_3$, in 50 ml of deionized water are fed into the reactor, and the suspension is held for 15 minutes. The pH is increased to 8.0 with 32% NaOH and the suspension is stirred again for 10 minutes. After filtering, washing and drying, the pigment (5 g) is calcined at a temperature of 700° C. for 5 minutes.

Example 8

The reaction process is the same as in Example 7 until the step of metered addition of $TiCl_4$. At this point, the pH is adjusted to 1.9 using 32% NaOH, and a solution of 33 g of $FeCl_3.6H_2O$ in 100 ml of deionized water is metered in over 2 hours, maintaining a pH of 1.9 using 32% NaOH solution. After stirring the suspension for 15 minutes, the pH is adjusted to 3.0 with 32% NaOH, and then 4.2 g of silane coupling agent in 50 ml of deionized water are fed into the reactor. The suspension is held for 15 minutes. The pH is increased to 8.0 with 32% NaOH and the suspension is stirred again for 10 minutes. After filtering, washing and drying, the pigment (5 g) is calcined at a temperature of 700° C. for 5 minutes.

Example 9

Sunscreen cream
Raw Materials

| A: | Liquid paraffin | 38.0 % |
|---|---|---|
|  | Cetanol | 1.5 |
|  | Beeswax | 6.0 |
|  | Stearic acid | 20.0 |
|  | POE (5,5) Cetyl ether | 1.5 |
|  | Sorbitan monostearate | 2.5 |
| B: | 10% NaOH | 1.0 |
|  | DI-water | 31.5 |
| C: | Glycerin | 6.0 |
|  | $TiO_2$ | 5.0 |
|  | $SiO_2$ coated $TiO_2$ | 5.0 |

Preparation $TiO_2$ and $SiO_2$ coated $TiO_2$ are dispersed in glycerin. A and B group are heated up seperately at 75° C., then the two mixtures are emulsified by high speed stirring. Lastly, mix the C group is mixed with emulsified A & B mixture at 50° C.

Example 10

An aqueous solution of titanium tetrachloride prepared from 50 ml of titanium tetrachloride and 500 ml of water (2,18 mol/l $TiO_2$) is heated to 60° C. with stirring. To the white $TiO_2$ suspension obtained is added dropwise 40 g (12 g as $SiO_2$) of colloidal silica sol, type XL, with a size distribution of 40 to 50 nm. The pH is increased to 2.0 with 32% NaOH solution with stirring, and 2 g of $CH_3Si(OMe)_2$ (silane coupling agent) in 50 ml of deionized water are added into the suspension, and the suspension is held for 15 minutes. The pH is increased to 8,0 with 32% NaOH solution and the suspension is stirred again for 10 minutes. After filtering, washing and drying the dried product is powdered by using a blender and the resulting powder (5 g) is calcined at 700° C. for 5 minutes.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A non-porous spherical $SiO_2$ particle having a diameter of 5 to 500 nm with a non-continuous coat of metal oxide, particles, wherein the metal oxide is $TiO_2$, or a mixture of $TiO_2$ and $Fe_2O_3$.

2. A particle according to claim 1, which is transparent to visible light in a concentration of 5% by weight in a medium containing (a) a copolymer of vinyl chloride and vinyl acetate, (b) xylene in a concentration of from 30 to 40% and (c) cyclohexanone in a concentration of from 50 to 60%.

3. A particle according to claim 1, which is transparent to visible light in a concentration of 1.5% by weight of the medium.

4. A particle according to claim 1, wherein the metal oxide particles are present in an amount of from 20 to 75% by weight.

5. A particle according to claim 1, having a mass ratio of $SiO_2$:metal oxide of 1:0.1 to 1:2.

6. A particle according to claim 1, wherein the metal oxide particles have a size of less than 60 nm.

7. A particle according to claim 1, wherein the $SiO_2$ particle coated with metal oxide is aftercoated with inorganic and/or organic compounds.

8. A particle according to claim 7, wherein the organic compounds are silanes of the formula $R_nSi(OX)_3$, in which $R_n$ is an alkyl group having 1 to 18 carbon atoms and X is an alkyl group having 1 to 2 carbon atoms.

9. A particle according to claim 8, wherein the silane is $CH_3Si(OMe)_3$.

10. A particle according to claim 7, wherein the inorganic compounds are metal oxides.

11. A particle according to claim 10, wherein the metal oxides are zinc oxide, iron oxide or zirconium oxide.

12. A particle according to claim 1, wherein the coated spherical $SiO_2$ particle has a diameter of less than 500 nm.

13. A process for the preparation of a particle according to claim 1, comprising adding to a suspension of spherical particles of $SiO_2$ a metal salt solution at a metering rate of about 0.0005–0.5 mg metal salt per minute per $m^2$ surface area of the $SiO_2$ particles.

14. A process according to claim 13, conducted at a pH of 1.3–2.5, wherein the coated particles are separated, dried and optionally calcined.

15. A process for the preparation of spherical $SiO_2$ particles according to claim 1, which are coated with a non-continuous layer of metal oxide particles, comprising heating an aqueous solution of titanium tetrachloride and adding the thus obtained $TiO_2$ heated solution dropwise to a suspension of spherical $SiO_2$ particles, thus forming a mixture having a pH lowering the pH to a value effective to coat the $SiO_2$ particles with $TiO_2$, whereupon a silane coupling agent is added to the suspension, and the pH value is increased to a value effective to couple the silane to the particles, and after filtering, washing and drying the coated $SiO_2$ particles, said particles are formed into a powder and the powder is calcined.

16. A process according to claim 13, wherein the spherical $SiO_2$ particles have a diameter of from 5 to 500 nm which are coated with a non-continuous layer of $TiO_2$ particles with a size of less than 60 nm, where spherical $SiO_2$ particles are dispersed in deionized water, an aqueous titanium salt solution is added to the dispersed particles at a metering rate of from 0.0005 to 0.5 mg of $TiO_2$ per minute and per $m^2$ surface area of the $SiO_2$ particles, thus forming a mixture having a pH, the pH being kept constant by simultaneous addition of a base, and the coated $SiO_2$ particles are separated off, washed, dried and optionally calcined.

17. A process according to claim 16, wherein the $SiO_2$ particles coated with $TiO_2$, optionally after drying, are aftercoated with inorganic and/or organic compounds.

18. A process according to claim 17, wherein the organic compounds are silanes of the formula $R_nSi(OX)_3$, in which $R_n$ is an alkyl group having 1 to 18 carbon atoms and X is an alkyl group having 1 to 2 carbon atoms.

19. A process according to claim 18, wherein the silane used is $CH_3Si(OMe)_3$.

20. A process according to claim 18, wherein the inorganic compounds used are metal oxides.

21. process according to claim 20, wherein the metal oxides are zinc oxide, iron oxide or zirconium oxide.

22. In a paint, printing ink, plastic or sunscreen agent comprising a pigment, the improvement wherein the pigment is a particle of claim 1.

23. A cosmetic formulation comprising $SiO_2$ particles according to claim 1.

24. A particle according to claim 1, wherein the coated spherical $SiO_2$ particle has a diameter of 5 to 100 nm.

25. In a sunscreen agent comprising a pigment, the improvement wherein the pigment is a particle of claim 1.

* * * * *